United States Patent
Koehler et al.

(10) Patent No.: US 10,945,690 B2
(45) Date of Patent: Mar. 16, 2021

(54) SCANNING X-RAY APPARATUS WITH FULL-FIELD DETECTOR

(71) Applicant: KONINKLIJKE PHILIPS N.V., Eindhoven (NL)

(72) Inventors: Thomas Koehler, Hamburg (DE); Gerhard Martens, Henstedt-Ulzburg (DE); Roland Proksa, Neu Wulmstorf (DE); Hanns-Ingo Maack, Norderstedt (DE); Udo Van Stevendaal, Ahrensburg (DE); Franz Josef Pfeiffer, Unterföhring (DE); Peter Benjamin Theodor Noel, Unterföhring (DE); Maximilian Von Teuffenbach, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 107 days.

(21) Appl. No.: 15/738,324

(22) PCT Filed: Jun. 24, 2016

(86) PCT No.: PCT/EP2016/064649
§ 371 (c)(1),
(2) Date: Dec. 20, 2017

(87) PCT Pub. No.: WO2017/001294
PCT Pub. Date: Jan. 5, 2017

(65) Prior Publication Data
US 2018/0177475 A1 Jun. 28, 2018

(30) Foreign Application Priority Data
Jun. 30, 2015 (EP) ..................................... 15174413

(51) Int. Cl.
*G03H 5/00* (2006.01)
*A61B 6/00* (2006.01)

(52) U.S. Cl.
CPC ............ *A61B 6/484* (2013.01); *A61B 6/4035* (2013.01); *A61B 6/4233* (2013.01);
(Continued)

(58) Field of Classification Search
CPC ... A61B 6/4035; A61B 6/4233; A61B 6/4291; A61B 6/4464; A61B 6/484; A61B 6/502;
(Continued)

(56) References Cited

U.S. PATENT DOCUMENTS 8,184,771 B2 *   5/2012   Murakoshi .............   A61B 6/484
                                                    378/62
8,826,949 B2 *   9/2014   Kent .......................   B67C 11/02
                                                    141/342
(Continued)

FOREIGN PATENT DOCUMENTS

EP      2168488 A1      3/2010
JP      2004325183 A    11/2004
(Continued)

OTHER PUBLICATIONS

Roessl, Ewald "Clinical Boundary Conditions for Grating-Based Differential Phase-Contrast Mammography", Philosophical Transactions A, vol. 372, Issue 2010, Mar. 2014.
(Continued)

*Primary Examiner* — Irakli Kiknadze
(74) *Attorney, Agent, or Firm* — Larry Liberchuk

(57) ABSTRACT

An X-ray imaging apparatus with an interferometer (IF) and an X-ray detector (D). A footprint of the X-ray detector (D) is larger than a footprint of the interferometer (IF). The interferometer is moved in scan motion across the detector
(Continued)

(D) whilst the detector (D) remains stationary. Preferably the detector is a 2D full field detector.

15 Claims, 11 Drawing Sheets

(52) U.S. Cl.
CPC ............ *A61B 6/4291* (2013.01); *A61B 6/502* (2013.01); *A61B 6/4464* (2013.01)

(58) Field of Classification Search
CPC ....... A61B 6/4452; A61B 6/542; A61B 6/582; A61B 6/587; A61B 6/588; A61B 6/589; A61B 6/00; A61B 6/032; A61B 6/06; A61B 6/5211; A61B 6/5264; A61B 6/486; A61B 6/5205; A61B 6/461; A61B 6/482; A61B 6/50; A61B 6/5258; A61B 6/4208; A61B 6/405; A61B 6/488; A61B 6/0414; A61B 6/4007; A61B 6/508; A61B 6/04; A61B 6/505; A61B 6/4441; A61B 6/487; A61B 6/54; A61B 6/0457; G21K 2207/005; G21K 1/06; G21K 1/067; G21K 2201/067; G21K 1/02; G21K 1/025; G21K 2201/06; G21K 1/04; G21K 1/043; G21K 1/10; G21K 5/04; G21K 7/00; G01N 23/041; G01N 23/20075; G01N 23/046
USPC ...................................................... 378/36, 62
See application file for complete search history.

(56) References Cited

U.S. PATENT DOCUMENTS

| | | | | |
|---|---|---|---|---|
| 8,859,977 | B2* | 10/2014 | Kondoh | G01B 11/14 250/370.08 |
| 9,046,466 | B2* | 6/2015 | Ouchi | G01N 23/041 |
| 9,123,451 | B2* | 9/2015 | Nagai | G21K 1/06 |
| 2007/0183559 | A1 | 8/2007 | Hempel | |
| 2009/0250592 | A1 | 10/2009 | Takeda | |
| 2010/0091936 | A1* | 4/2010 | David | A61B 6/032 378/4 |
| 2013/0010926 | A1* | 1/2013 | Tada | A61B 6/4291 378/62 |
| 2016/0035450 | A1* | 2/2016 | Date | G21K 1/067 378/36 |

FOREIGN PATENT DOCUMENTS

| | | |
|---|---|---|
| JP | 2007330530 A | 12/2007 |
| WO | 2009076700 A1 | 6/2009 |
| WO | 2012057047 A1 | 5/2012 |
| WO | 2014002026 A1 | 1/2014 |
| WO | 2014030115 A1 | 2/2014 |

OTHER PUBLICATIONS

Koehler, Thomas et al "Slit-Scanning Differential X-Ray Phase Contrast Mammography: Proof-of-Concept Experimental Studies", Medical Physics, vol. 42, 1959.

Xi, Yan et al "Fast Grating Based X-Ray Phase Contrast Tomosynthesis", 35th Annual International Conference on the IEEE EMBS, Jul. 2013.

Li, Ke et al "Grating-Based Phase Contrast Tomosynthesis Imaging: Proof of Concept Expermiental Studies", Medical Physics, vol. 41, 2014.

Meinel, F. et al "Improved Diagnosis of Pulmonary Emphysema Using In Vivo Dark-Field Radiography", Investigative Radiology, vol. 49, No. 10, 2014.

Kottler, C. et al "Grating interferometer based scanning setup for hard x-ray phase contrast imaging", Review of Scientific Instruments vol. 78, 2007.

* cited by examiner

SCANNING X-RAY APPARATUS WITH FULL-FIELD DETECTOR

CROSS-REFERENCE TO PRIOR APPLICATIONS

This application is the U.S. National Phase application under 35 U.S.C. § 371 of International Application No. PCT/EP2016/064649, filed on Jun. 24, 2016, which claims the benefit of European Patent Application No. 15174413.3, filed on Jun. 30, 2015. These applications are hereby incorporated by reference herein.

FIELD OF THE INVENTION

The invention relates to an X-ray imaging apparatus.

BACKGROUND OF THE INVENTION

Grating-based differential-phase contrast imaging and dark field imaging are promising technologies that add diagnostic value in particular in the area of chest imaging since the dark field signal channel is highly sensitive to changes of the micro-structure of lung tissue.

Different systems have been proposed on the past. However some of these systems are still relatively expansive due to the required component performance. For instance, full field systems (see for instance Ewald Roessl, "Clinical boundary conditions for grating-based differential phase-contrast mammography" in Philosophical Transactions A, 6 Mar. 2014, volume 372, issue 2010) have good flux properties and afford relatively quick data acquisition but require large grating structures, which imply high cost and difficult alignment procedures.

SUMMARY OF THE INVENTION

There may therefore be a need for alternative X-ray imaging apparatus.

According to a first aspect of the invention there is provided an X-ray imaging apparatus comprising:

an X-ray source (XR) for emitting a beam of X-ray radiation;

an X-ray detector (D) arranged opposite said X-ray source across an examination region for accommodating an object to be imaged; and an interferometer (IF) arranged, at least partly in the beam of X-ray radiation during operation for performing differential phase contrast imaging and/or dark field imaging, between the X-ray source (XR) and the X-ray detector, the interferometer (IF) comprising at least one grating (G1) to modulate onto said X-ray radiation an interference pattern detectable by said X-ray detector;

wherein a footprint of said at least one grating is smaller than a footprint of a radiation sensitive area of said X-ray detector; and wherein the apparatus is configured to effect, during an imaging operation, said at least one grating to move in a scanning motion relative to the X-ray detector whilst said X-ray detector remains stationary relative to the examination region.

In other words, it is proposed herein to use a relatively large X-ray detector (possibly a full field X-ray detector) in combination with a relatively small (that is, compared to the field of view of the X-ray detector) interferometer, which interferometer during an imaging operation is being moved by the apparatus across the field of view for scanning purposes. Since the detector pixels are not moving during said imaging operation, the X-ray imaging apparatus advantageously prevents from motion blur in full. Accordingly, an expensive X-ray detector providing for a high detector read-out, which would ordinarily be required in prior art scanning systems for suppressing motion blur, is effectively circumvented by the X-ray imaging apparatus according to the present invention. Consequently, contrary to prior art scanning systems in which scanning time is inversely proportionally related to the detector read-out, in the X-ray imaging apparatus according to the present invention scanning time is related to the speed at which fringes, as generated by the interferometer during operation, move across the X-ray detector. This enables a shorter scan time which is notably beneficial for mammography during which the breast is held in painful compression hence in view of which scan time should be kept at a minimum. For instance, given a reasonable dimension (in the scanning direction) of the interferometer of about 40 mm, it is then reasonable for a scanning system that two fringe periods are generated across these 40 mm. With a modest readout in the order of eight readouts per fringe period, one can achieve a readout for every 2.5 mm of scan motion, which is more than an order of magnitude less demanding than in prior art scanning systems. This is because in an prior art scanning system, the detector moves as well and a readout is required at the rate at which the X-ray detector moves over a distance equal to the pixel size, which is typically in the order of 50 μm (in case of mammography) to 200 μm (in case of radiography).

In addition the apparatus for X-ray imaging effectively arranges, compared to prior art scanning systems, that each and every ray of the beam of X-ray radiation is impacting only a respective single detector pixel of the X-ray detector during the entire imaging operation. In other words, there is a rigid coupling between rays on the one hand and detector pixels on the other. Obviously, one detector pixel will be impacted by a plurality of rays.

Another effect of the X-ray imaging apparatus is that grating tiling, which would ordinarily be required to constitute a composite grating having a footprint equal to the footprint of the X-ray detector, is effectively avoided. That is, the X-ray imaging apparatus employs a grating module whose footprint may only be a fraction of the footprint of the X-ray detector.

In this text, "optical axis" is an imaginary line that defines the path along which the central X-ray beam during operation propagates from the X-ray source towards the X-ray detector, and along which the beam of X-ray radiation exhibits some form of symmetry.

It envisaged herein that the object, e.g. a patient, remains stationary (at least relative to the X-ray detector) during data acquisition, that is, whilst the apparatus causes the interferometric grating to perform the scan motion and whilst radiation is emitted from the X-ray source. Of course, this does not exclude some embodiments where the X-ray imaging apparatus in arranged for moving the object, e.g. a patient, relative to the X-ray detector between any data acquisitions.

According to one embodiment of the X-ray imaging apparatus, one dimension of the footprint of the at least one grating is essentially coextensive with a corresponding dimension of the footprint of the X-ray detector. Herein, "a corresponding dimension" means a dimension in a substantially parallel direction.

According to another embodiment of the X-ray imaging apparatus, the X-ray detector is a full-field X-ray detector. The X-ray detector is preferably planar but curved arrangements are not excluded herein. In particular, in this example detector pixels of the X-ray detector are arranged in a two-dimensional layout.

According to another embodiment of the X-ray imaging apparatus, the X-ray imaging apparatus is configured to effect, different from the scanning motion, another motion of the at least one grating. In addition, or in the alternative, the apparatus is configured to effect, a motion of the object relative to the at least one grating. Both examples allow imaging of objects having a size either larger than the field of view of the X-ray detector or larger than the interferometer footprint.

According to another embodiment of the X-ray imaging apparatus, the interferometer includes a further, second, grating, said second grating likewise movable in the scanning motion, wherein the at least two gratings remain in a fixed spatial relationship relative to each other during the scanning motion. Herein, the second grating may be an analyzer grating i.e. an absorption grating which enables softening the requirements on the spatial resolution of the X-ray detector for the purpose of adequately resolving an interference pattern generated by the at least one grating when interacting with the beam of X-ray radiation during operation.

According to another embodiment of the X-ray imaging apparatus, the gratings are arranged on mutually opposite sides of the examination region. This example provides for the so-called "inverse geometry" for differential phase contrast imaging and/or dark field imaging. Such inverse geometry is advantageous in that it softens the requirements on the spatial resolution of the X-ray detector for the purpose of adequately resolving an interference pattern generated by the at least one grating when interacting with the beam of X-ray radiation during operation.

According to another embodiment of the X-ray imaging apparatus, the gratings are arranged on mutually same side of the imaging region. This example enables the so-called "conventional geometry" for differential phase contrast imaging and/or dark field imaging.

According to another embodiment of the X-ray imaging apparatus, the scanning motion is along a straight path.

According to another embodiment of the X-ray imaging apparatus, the scanning motion is along a curved or arcuate path.

According to another embodiment of the X-ray imaging apparatus, the X-ray detector module has a monolithic structure.

According to another embodiment of the X-ray imaging apparatus, the X-ray source is arranged to move, relative to the object, along a path substantially parallel to the scanning motion. This example provides for an inclined projection of the object at the X-ray detector and accordingly affords tomosynthesis imaging capability. In this text, "substantially parallel" is understood to mean parallel including minor deviations thereof up to ±5 degrees as may be due to tolerances caused by e.g. manufacturing and installation of the apparatus. Likewise, in this text "substantially perpendicular" is understood to mean perpendicular including minor deviations thereof up to ±5 degrees as may be due to tolerances caused by e.g. manufacturing installation of the apparatus. According to another embodiment of the X-ray imaging apparatus, the apparatus further comprises a plurality of source gratings arranged in a series substantially parallel to path along which the X-ray source is movable. This example enables moving only the X-ray source for the purpose of tomosynthesis imaging, i.e. maintaining the plurality of source gratings in a stationary position while performing tomosynthesis imaging. Therefore this example is advantageous in that it significantly softens the accuracy requirements for the movement of the X-ray source along the path compared to a simultaneous movement of the X-ray source and a source grating along said path.

According to another embodiment of the X-ray imaging apparatus, the scanning motion is vertical or horizontal. In this text, "horizontal" means a direction substantially perpendicular to gravity. Likewise, in this text, "vertical" means a direction substantially parallel to gravity. This example has the effect of enabling imaging an object, e.g. a patient, in a standing position or a lying position, respectively.

According to another embodiment of the X-ray imaging apparatus, rulings of the at least one grating extend in a direction substantially parallel to the scanning motion or substantially perpendicular to said motion.

According to another embodiment of the X-ray imaging apparatus, the X-ray imaging apparatus is further configured to effect, during an imaging operation, the at least one grating to move in the scanning motion relative to the X-ray detector to such extent that said at least one grating is not impacted by the beam of X-ray radiation during operation. This example has the effect of enabling switching from differential phase contrast imaging and/or dark field imaging to conventional radiology i.e. projection imaging, and vice versa.

The X-ray imaging apparatus according to the present invention allows for useful application in a clinical environment such as a hospital. More specifically, the present invention is very suitable for application in imaging modalities such as mammography, diagnostic radiology and interventional radiology for the medical examination of patients. In addition, the present invention allows for useful application in an industrial environment. More specifically, the present invention is very suitable for application in non-destructive testing (e.g. analysis as to composition, structure and/or qualities of biological as well non-biological samples) as well as security scanning (e.g. scanning of luggage on airports).

BRIEF DESCRIPTION OF THE DRAWINGS

Exemplary embodiments of the invention will now be described with reference to the following drawings wherein.

DETAILED DESCRIPTION OF EMBODIMENTS

With reference to the following drawings we propose a new type of X-ray imaging apparatus. The X-ray apparatus is capable of multi-channel imaging, that is, it is not only capable of imaging for spatial distribution of absorption of or in an object OB but also for the spatial distribution of refraction (phase contrast imaging) and/or for the spatial distribution of small angle scattering (dark field imaging). This type of imaging capability is sometimes referred to a DPCI (differential phase contrast imaging), but, again, it is of course not only the phase contrast one can image for but also for images as per the other two channels. Very briefly, the newly proposed X-ray imaging apparatus has a grating based interferometer that is scannable across a stationary X-ray detector.

Figure 1:
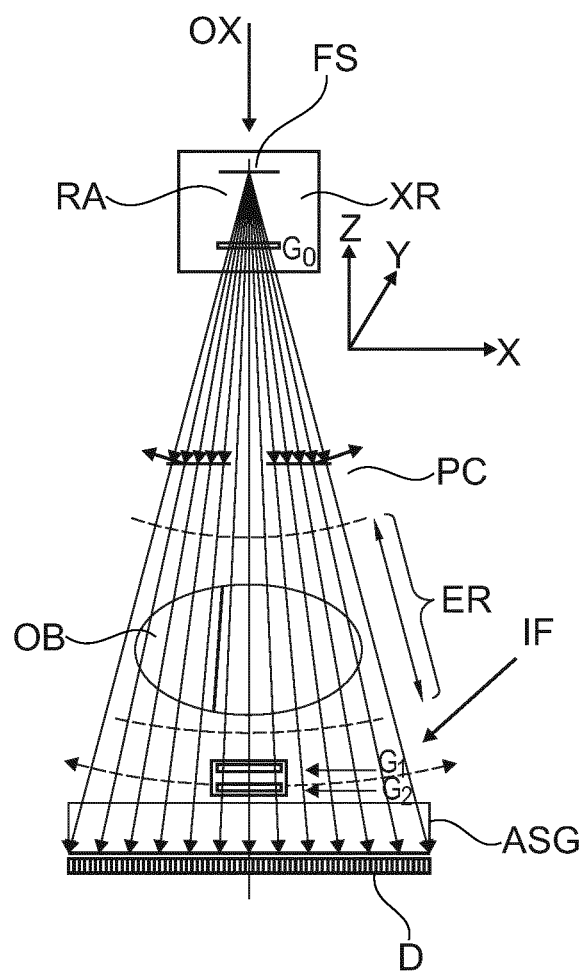
FIGS. 1-6 show embodiments of an X-ray imaging apparatus with stationary X-ray detector and curved grating scan paths.

Reference is now made to FIG. 1 where an embodiment of the newly proposed imaging apparatus is schematically shown. We will also use FIG. 1 to introduce certain basic imaging components some of which will be featured across the remaining embodiments with like reference symbols indicating like components.

With continued reference to FIG. 1, but in more detail, the multi-channel imaging capability is afforded by the interferometer IF built into the X-ray imaging apparatus.

In one embodiment, the interferometer IF comprises two grating structures G1 and G2 although, as will be mentioned below, single grating interferometers (having only a single grating G1) are not excluded herein and will be described later below. In the specific case of a single grating interferometer IF, the X-ray detector D preferably has a pitch sufficiently small, hence a spatial resolution sufficiently large, for detecting i.e. adequately resolving the interference pattern generated by the grating G1 for the purpose of differential phase contrast imaging and/or dark field imaging. For that purpose the X-ray detector may be a high resolution X-ray detector known per se having a spatial resolution of 50 micrometers or more.

The grating G1 is either an absorption grating or phase shift grating whereas G2 is an absorption gating. The gratings are manufactured by photo lithographically processing suitable substrates such as a silicon wafer (rectangular or even square shaped but other shapes may also be called for in other contexts). A pattern of periodic rulings is formed in those silicon "cards" formed by trenches of different aspect ratio. The trenches may be filled with suitable filling material such as gold or other. The ruling patterns are preferably one dimensional but may also be two dimensional such as to confer a checker board pattern. In the 1D example the rulings extend only in one direction across the surface of the silicon card. Include modules here:

The X-ray imaging apparatus further comprises an X-ray source XR and the X-ray detector D. Preferably the X-ray detector D is a 2D full view X-ray detector either planar or curved. Alternatively the X-ray detector D may also be arranged as a plurality of discreetly spaced individual lines of detector elements. Such X-ray detector is referred to as a "line detector". Preferably however the X-ray detector is a "true" 2D structure where a plurality of detector pixels are arranged in rows and columns as an array to form a 2D X-ray radiation sensitive surface capable of registering X-ray radiation emitted by the X-ray source.

The X-ray detector D and the X-ray source are spaced apart to form an examination region ER. The examination region is suitably spaced to receive the object OB to be imaged. The object may be inanimate or animate. For instance the object may be a piece of luggage or other sample to be imaged such as in non-distractive material testing etc. Preferably however a medical context is envisaged where the (animate) "object" is a human or animal patient or is at least an anatomic part thereof as it not always the case that the whole of the object is to be imaged but only a certain anatomic region of interest. For simplicity we will refer hereinafter to the object OB as "patient OB", with the understating that non-medical applications of the proposed imager are not excluded herein.

The interferometric grating structures G1 and G2 are arranged in the examination region ER between the X-ray source XR and X-ray detector D. More specifically, the X-ray source XR has a focal spot FS from which the X-ray radiation beam emerges. It is the space between the focal spot FS and the X-ray detector's radiation sensitive surface where the two or three grating structures are arranged. It will be convenient in the following to refer to the grating G1 as the phase grating and to grating G2 as the analyzer grating. In some embodiments, there is in addition to the interferometric gratings G1, G2 of the interferometer IF, a further grating G0 which we will be referred to as the source grating.

The source grating G0 is arranged in proximity of the X-ray source for instance is arranged at the egress window of a housing of the actual X-ray tube. The function of the source grating G0 is to make the emitted radiation at least partly coherent. In other words, the source grating G0 can be dispensed with if an X-ray source is used which is capable of producing native coherent radiation.

The multi-channel imaging capability is now conferred by the interferometer IF briefly as follows: The at least partly coherent radiation passes through the examination region ER and interacts with the object OB therein. The object then modulates attenuation, refraction, and small angle scattering information onto the radiation which can then be extracted by operation of the grating tandem G1 and G2. More particularly the gratings G1, G2 induce an interference pattern which can be detected at the X-ray detector D as fringes of a Moiré pattern. Yet more particularly, if there was no object in the examination region there would is still an interference patter observable at the X-ray detector D, called the reference pattern which is normally captured during a calibration procedure. This comes about by especially adjusting or "de-tuning" the mutual spatial relationship between the two gratings G1 and G2 by inducing a slight flexure for instance so that the two gratings are not perfectly parallel. Now, if the object is resident in the examination region and interacts with the radiation as mentioned, the Moiré pattern, which is now more appropriately called the object pattern, can be understood as a disturbed version of the reference pattern. This difference from the reference pattern can then be used to compute one or all of the three images (attenuation, phase contrast, dark field). Yet more particularly, to be able to acquire suitable signals from which the images can be computed, a scanning motion is performed by the grating tandem G1-G2. As a result of this motion, at each pixel of the X-ray detector D a series of intensity values are detected. For good results, the detuning of the gratings G1, G2 is such that a period of the Moiré pattern should extend for a few of its cycles (two or three) in direction of the scan motion. For each X-ray detector pixel, the series of intensity values can then be fitted to a (sinusoidal) signal forward model for instance to so derive the respective contributions of refraction, absorption, and small angle scatter. This type of signal processing is done in a signal processing unit not shown in FIG. 1 and has been described elsewhere. In a radical departure from previous phase contrast and/or dark field signal imaging approaches, in the present embodiments as proposed herein the X-ray detector D remains stationary throughout the examination. More particularly the X-ray detector D remains stationary for any given orientation of the optical axis OX which is shown in FIG. 1 to extend along the Z axis. In yet other words, it is proposed herein to keep the X-ray detector D stationary (at least during an image acquisition operation) with respect to an arbitrary reference point in the examination region. The interferometric setup as described above is what is commonly referred to as a Talbot-Lau interferometer. The distances between G0 and G1 and between G1 and G2 must be finely tuned to fit the requirements of Talbot distance which in turn is a function of the "pitch" (that is, the spatial period of the grating rulings) of the respective grating. Moving the interferometer IF relative to the X-ray detector D may cause a slight change in fringe distribution due to fringe drift. However, in a specific example, the fringe drift is compensated by relating such drift to the fringe drift as obtained with a reference scan. Such reference scan may be a blank scan performed at the installation of the X-ray imaging apparatus.

As mentioned, the motion for the collection of the necessary measurement when sampling the interference pattern is achieved by the scanning operation of the gratings G1 and G2. In one embodiment, the interferometer IF is essentially a "grating pack" with the two gratings G1 and G2 are fixedly mounted with respect to each other in a suitable frame or cage and this frame is fixedly arranged in a scan arm GT or other moveable gantry structure (not shown in FIG. 1). The arm, and with it the interferometer IF performs a pendulum like motion across the X-ray detector surface. The pivot point for the scan arm motion runs through the focal spot FS of the X-ray source but may not be so in all embodiments. The gratings G1 and G2 of the interferometer IF are held in fixed spatial relationship with respect to each other at all times during the scan motion and remain essentially parallel, or at least in a fixed spatial relationship, to G0. Suitable tracking circuitry (not shown) correlates interferometer position with X-ray detector pixel position to timely trigger a sequence of read-out burst to make sure each pixel is supplied with the above mentioned series of measurements to correctly sample the interference pattern.

In order to keep production costs low, it will be appreciated that the footprint of the interferometer, more specifically, the area occupied by the gratings G1 and/or G2 is smaller than the radiation sensitive surface area of the X-ray detector D. For instance in FIG. 1, when viewed along the optical axis, the footprint of both gratings is only a fraction of the X-ray detector width, such as only half as wide, quarter, ⅛th, etc. In FIG. 1, the X-Y plane is the X-ray detector plane with X, Y designating the direction of pixelation in the X-ray detector D. In the embodiment of FIG. 1 (but not necessarily in all embodiments) it is also the X-ray source that rotates around the focal point that passes through the focal spot FS. The rotation axis RA for scan arm an X-ray source extends into the paper plane of FIG. 1 (along the Y direction). Having the X-ray source rotate in concert with the pendulum motion of the grating tandem G1, G2 allows increasing flux.

According to one embodiment there is also a pre-collimator arranged between the X-ray source and the patient OB so as to conform the radiation beam to the dimensions or footprint of the gratings G1 and/or G2. The collimator PC moves in concert with the pendulum motion of the interferometer IF during the image acquisition. One way to achieve this is to mount the collimator to the scan arm GT proximate to the source grating G0 at an appropriate distance.

In the embodiment of FIG. 1 it is also the source grating G0 which moves in concert with the swinging scanning motion of the grating pack G1, G2 so as to remain parallel at all times during the rotational scan motion. One way to do this is to mount the grating in the scan arm.

As shown in FIG. 1, an anti-scatter grid ASG may be arranged between the interferometer and the X-ray detector surface.

Figure 2:
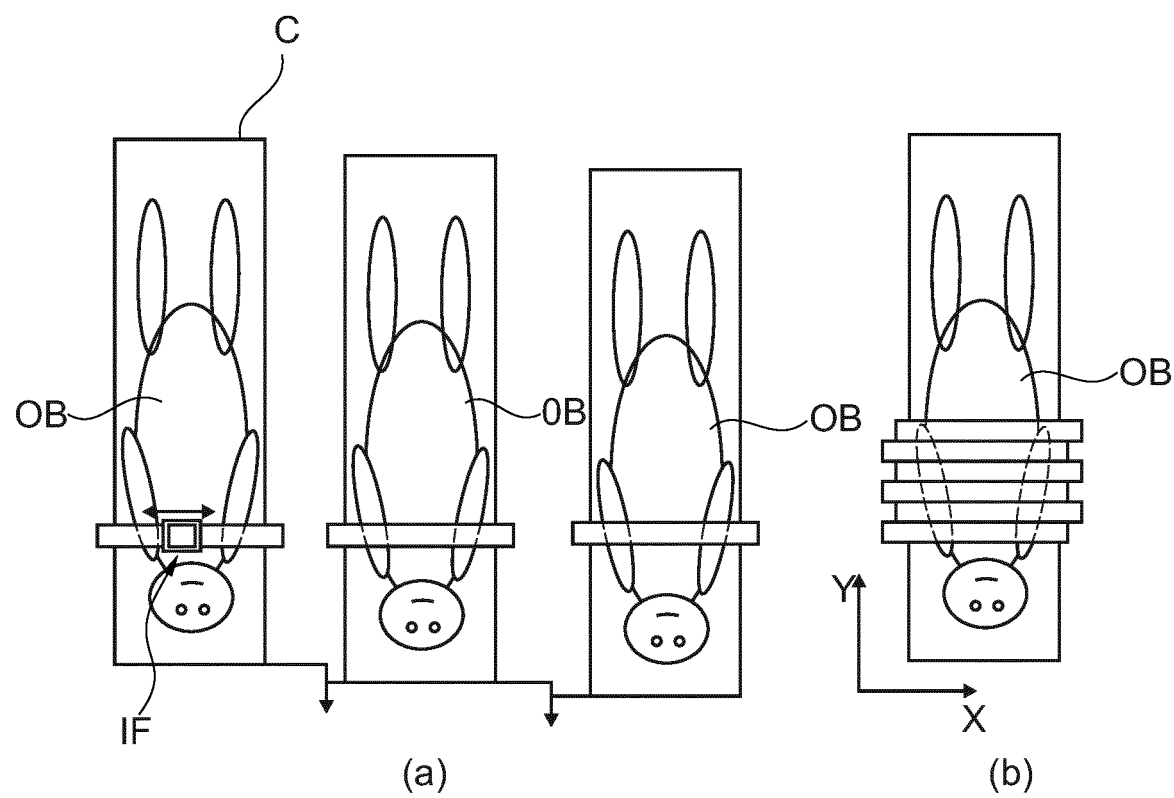

In the embodiment of FIG. 1 it is envisaged that the patient OB lies on an examination table or couch C (not shown in FIG. 1 but see FIG. 2) during the image acquisition. In other words the patient's longitudinal axis extends into the drawing plane as per FIG. 1 whilst the pendulum motion of the gratings G1, G2 (and that of G0) swings in a vertical plane with the patient's longitudinal axis (in FIG. 1 extending into the Y direction) extending into the paper plane of FIG. 1.

The mutually rigidly mounted gratings G1, G2 move the full length from one X-ray detector edge to the opposing X-ray detector edge if a full field image is desired, i.e. an image that is as wide in scan direction as the X-ray detector itself. If the user requests a smaller FOV (field of view), however, a reduced scan range can be used to minimize the acquisition time. In the drawings of FIG. 1 the two opposing edges extend into the Y direction with the scanning sweep action proceeding in the X direction perpendicular thereto.

More particularly, and as will be clear in FIG. 1 to ensure that it is also the pixels at the edge portion of the X-ray detector D that receive sufficient amount of serial intensity measurements, the interferometer IF will, in its scan motion, even slightly swing outside the X-ray detector surface area, that is, beyond the two opposing edges of the X-ray detector. Although not necessarily so in all embodiments, (see for instance FIG. 3) both dimensions, that is, length and width of the gratings G1 and G2 are smaller than the respective length and widths of the X-ray detector plane.

More particularly, each of the two gratings G1 and G2 may be formed from a single grating module. That is, in one embodiment, at least one or, preferably, both the gratings G1, G2 are each formed from a monolithic piece of rectangular or square wafer. Again this allows cost savings as expensive tiling solution (where plurality of such module are joined together) are not necessary although such tiling is not excluded and specifically envisaged in some of the embodiments. This situation is depicted in plan view as per (a) of FIG. 2 (viewed along the optical axis OX in Z direction). In one embodiment, to be able to image a larger region of interest, the patient couch C with the patient OB thereon is advanced by a suitable actuator in Y or X direction, that is, along one of the edges of the X-ray detector D. During this motion of the couch C the interferometer G1, G2 (shown as a hatched rectangle in (a)) is moved as described above in scan motion to scan the X-ray detector sensitive surface from X-ray detector edge to X-ray detector edge so as to scan, in effectively a meandering fashion, the desired region of interest. In other words, the scanning operation is performed in multiple "tracks" each shown as horizontal bars in FIG. 2. In one embodiment, the shuttling of the interferometer grating pack G1, G2 of the interferometer IF between the X-ray detector edges in the scanning operation can be performed whilst the couch is advanced past the X-ray detector. Preferably and alternatively, to reduce motion blur, in another embodiment, the two motions, that is, the interferometer scan motion G1, G2 and the couch motion, are interlaced. That is, there is, say, first a scanning motion across the X-ray detector plane in one direction to collect measurements in a first track. The interferometer then rests there. The couch is then advanced and then the interferometer IF returns in the opposite direction to the other edge to scan the second track, and so on. As a variant to FIG. 2 the relative motion between the interferometer IF and the patient can also be achieved by having the scan arm arranged to move in a second motion perpendicular to the motion as per the scan direction. So rather than having the couch advance past the X-ray detector it is the scan arm that can move and swing not only across the width of the X-ray detector but can also move in a direction perpendicular thereto. In other words, the swing plane of the scan arm GT can be shifted along the patient's axis. The "strip" images reconstructed from the data collected in the different tracks, can then be combined as schematically shown per (b) into a super-image to cover the desired region of interest.

Figure 3:
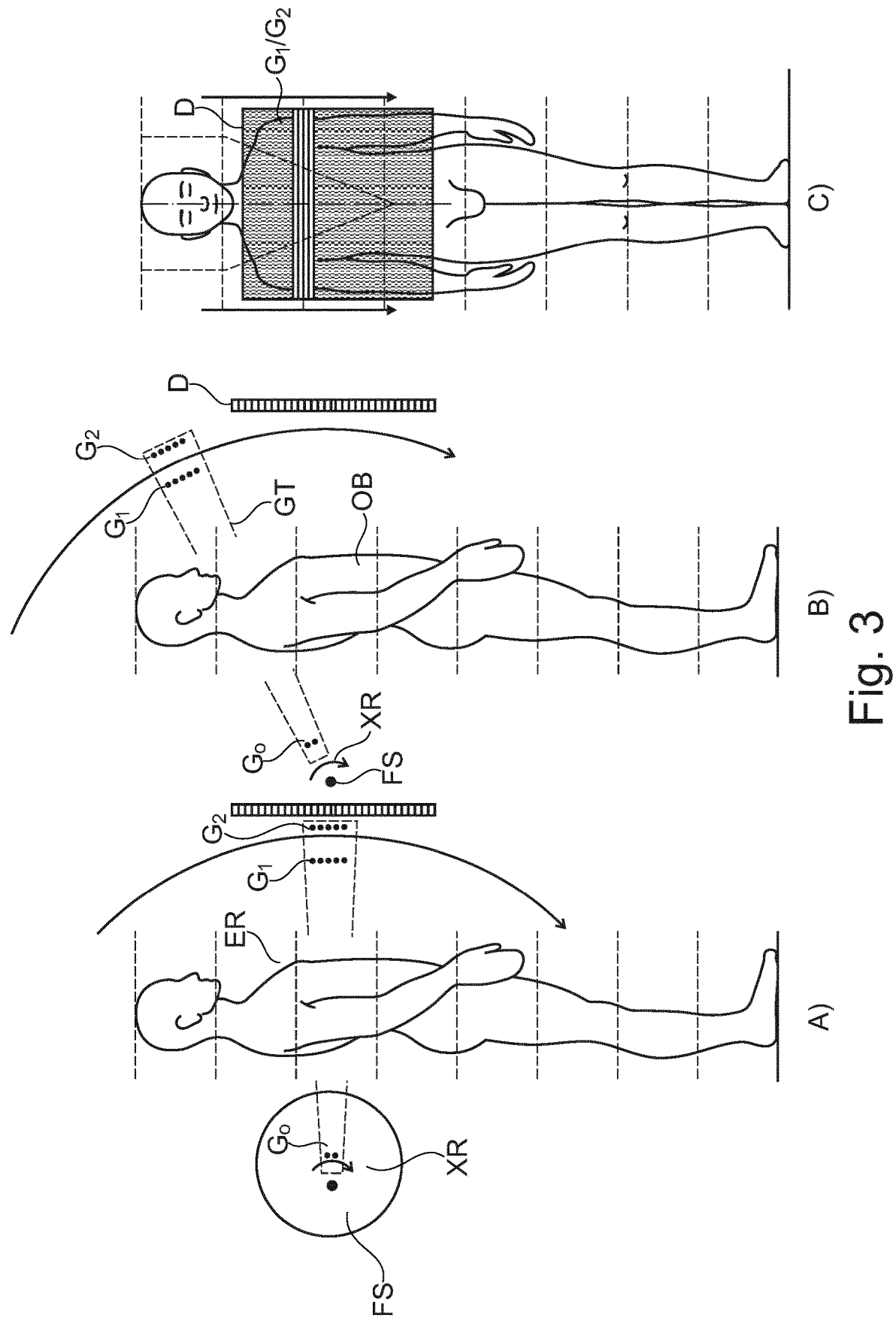

Reference is now made to FIG. 3, showing a different embodiment configured to allow the patient to stand (upright) during the X-ray imaging acquisition. This construction may be beneficial for chest imaging. Views A, B represent side elevations of the arrangement whilst view C is a frontal view through the X-ray detector D towards the X-ray source XR, that is, along the optical axis OX. Compared to FIG. 1 the optical axis in the FIG. 3 embodiment is effectively rotated by 90° in other words the interferometer IF now performs a curved scan motion in a vertical direction (relative to the ground of the examination room) from top to bottom or from bottom to top. This is indicated in frontal view C by the arrows showing a (downward) movement of the interferometer IF during operation. Although not necessarily so in all embodiments, in FIG. 3 the gratings G1, G2 of the interferometer IF is now essentially arranged as strip grating that are co-extensive of the width of the X-ray detector perpendicular to the scanning motion. Again gratings G1, G2 may be formed monolithically from single long wafer or substrate. However, in other embodiments, the strip arrangement can be achieved by tiling, that is joining together a plurality of smaller individual monolithic grating modules. The X-ray detector may be suspended in a fixture from the ceiling of the examination room or may be mounted on a floor mounted stand. The gratings G1 and G2 are rigidly mounted to a scan arm GT. Equally, the scan arm GT may be floor or ceiling mounted. The side views of Figure A and B show different instances during the scanning motion of the scan arm GT as it is moving along the vertical scan path in a circular or at least arcuate motion. Again, although not necessarily in all embodiments, the source grating G1 is arranged to rotate in concert about the focal spot FS. One way to do this is to have all three gratings arranged in the scan arm to maintain a fixed and parallel relationship during the vertical up or down motion. In FIG. 3 and in the following drawings, parts that move simultaneously or in concert are shown in the dashed box representing the scan arm GT.

Figure 4:
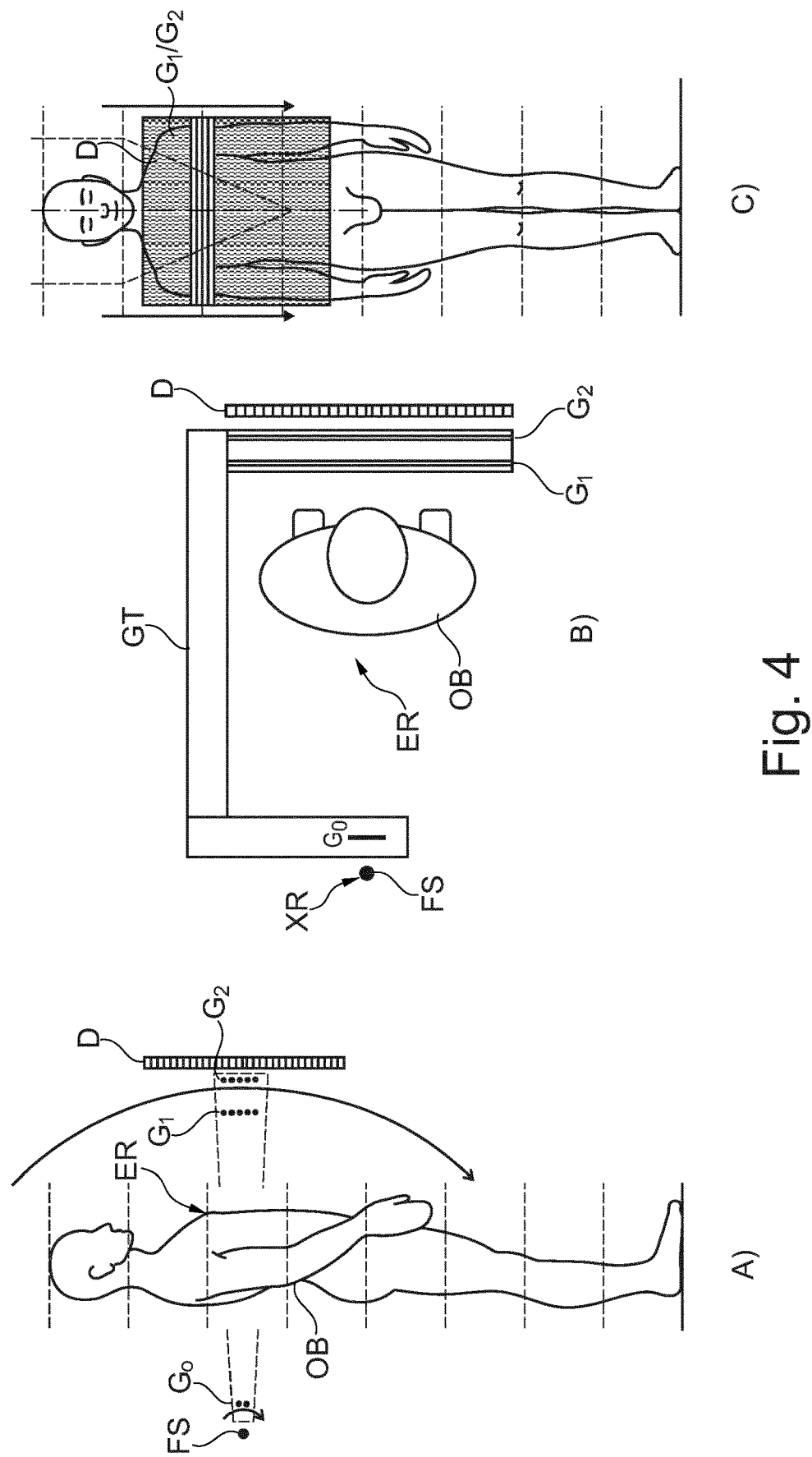

Reference now is now made to FIG. 4 which is similar to FIG. 3 except it includes a plan view B of the imaging apparatus. As can be best seen in this view B, in one embodiment, the scan arm GT is essentially C shaped so as to partly embrace the examination region and hence the patient OB. The scan arm has a cantilever structure and is arranged pivot in a vertical plane around the focal spot FS to fully scan the X-ray detector D from top to bottom. In this vertical scan direction embodiment it must be ensured that scan arm GT is manufactured from a material with sufficient rigidity to, if not to preclude, but at least ensure that any mechanical giving such as buckling or bending is kept to an acceptable minimum to avoid or reduce artifacts. Again, in the embodiment as per FIGS. 3 and 4, the X-ray tube XR itself may rotate around the rotation axis through its focal point although this is optional and may not be so in all embodiments. In other words, in one embodiment the X-ray source remains stationary whilst the scan arm performs its scan operation. Also in embodiments as per FIGS. 3 and 4 the arrangement of the interferometer IF as a strip that runs from X-ray detector edge to X-ray detector edge is but one embodiment. Just like in the embodiments in the FIG. 1 or FIG. 2, the interferometer IF may be smaller than the X-ray detector plane in both dimensions X and Y. More particularly, a grating pack formed from a single monolithic module for G1 and G2, respectively, is also envisaged in the FIGS. 3 to 4 embodiments. In this case however a more complex scan arm GT, suitably articulated, not unlike a robotic arm, may be used to trace out a meandering scan path in X and Y direction.

Figure 5:
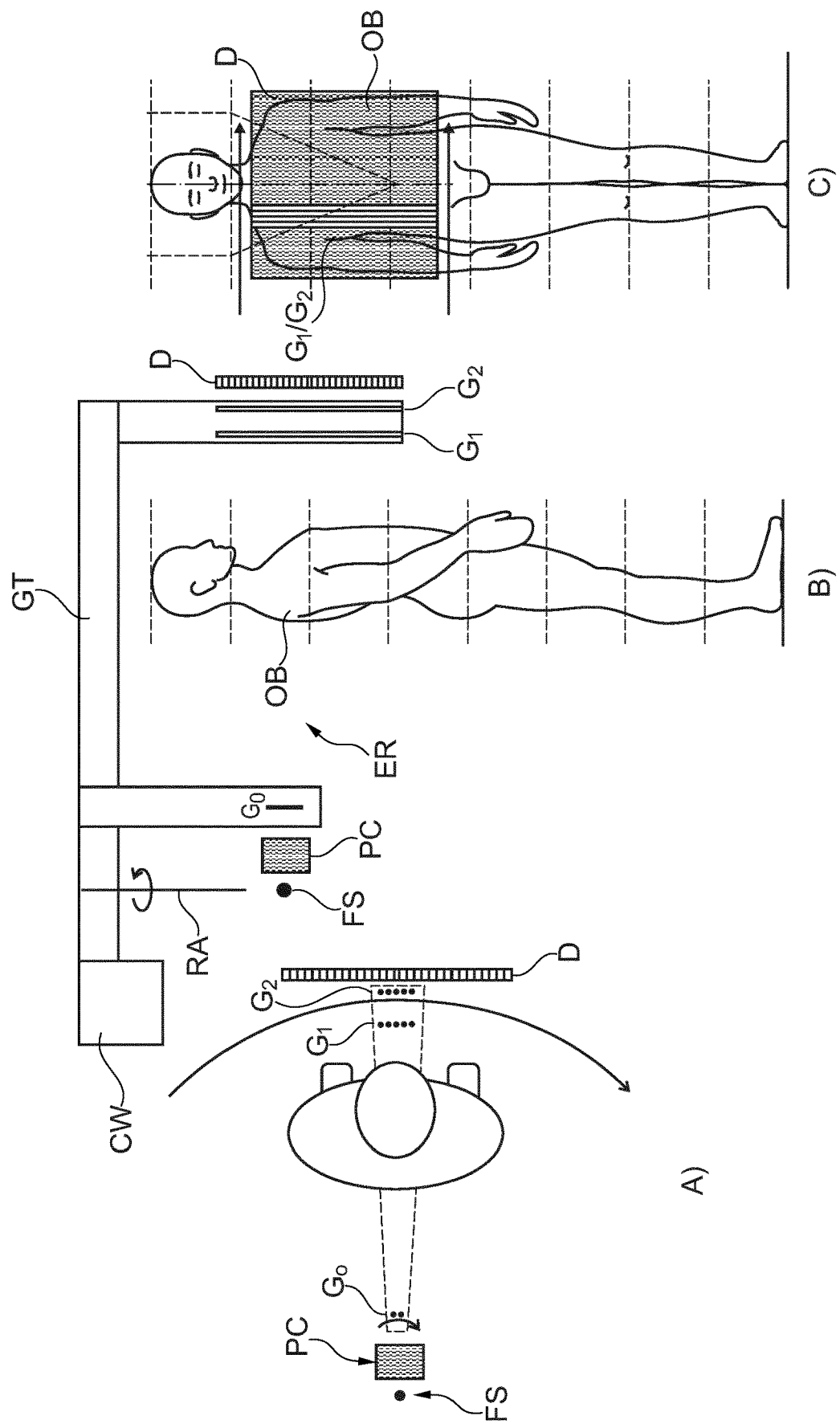

Reference is now made to the FIG. 5 embodiments, where views A, B, C correspond to a plan view, side elevation and frontal view, respectively. The arrangement is similar to that in FIGS. 3 and 4, but now the curved or arcuate scanning path is along a horizontal direction. In other words, during a scan the grating pack G1, G2 sweeps past the X-ray detector plane from left to right or right to left. In this embodiment the gantry is preferably ceiling-mounted, rotatable about rotation axis parallel to the longitudinal axis of the patient OB during the scan. Floor-mounted solutions are also envisaged. The X-ray source may be rotatable in concert with the gantry arm but may also remain stationary as shown here with pre-collimator arranged between the focal spot and source grating. As in the previously described embodiments, there may be pre-collimator that rotates in concert with the gratings so as to ensure that the beam is conformal with the footprint of the grating pack G1, G2. As before the collimator may be set up as one or more slit running perpendicular to one of the edges of the X-ray detector D for instance in X or Y direction. The horizontally rotatable scan arm GT is connected to a counter weight CW across the other side of the rotation axis to ensure smooth and stable operation. The ceiling suspended gantry GT is envisaged in one embodiment to be height adjustable so as to be able to position the X-ray detector at the desired region of interest.

Figure 6:
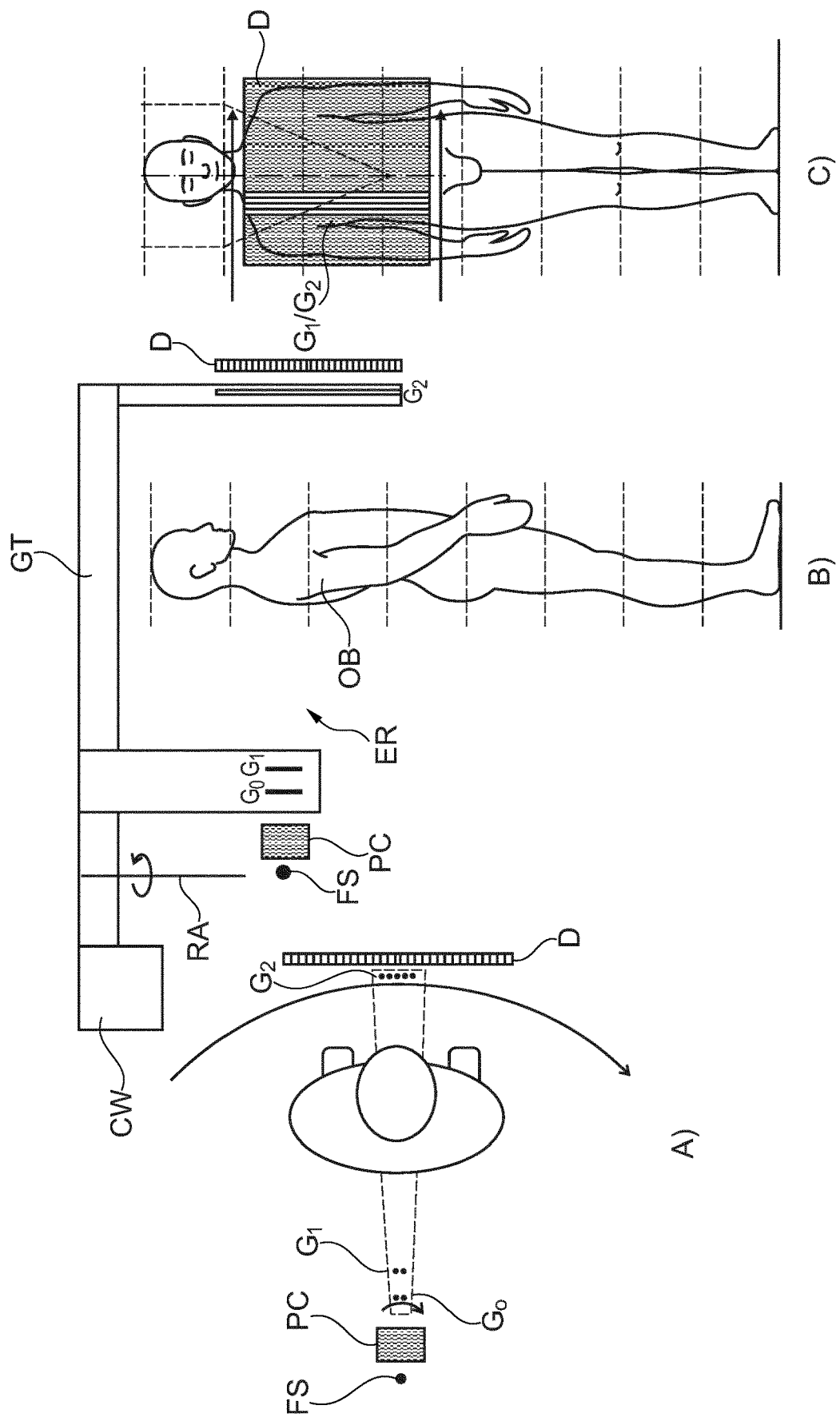

Referring now to FIG. 6, this embodiment is similar to embodiments as per FIGS. 3 and 4 but now an inverse geometry of the grating is used. In other words, phase grating G1 is now no longer rigidly mounted onto analyzer grating G2 but instead is rigidly mounted to, or at least relative to, source grating G0. In other words, the examination region ER is now "sandwiched" between the two gratings G1 and G2 and is not, as before, outside the grating pack G1, G2 of the interferometer. The inverse geometry option as per FIG. 6 allows securing a number of advantages for instance it affords flexibility for adjusting dark field sensitivity. A reduction of sensitivity is done by reducing the distance between patient OB and G2; in the embodiment as per FIGS. 3 and 4, a reduction would be achieved by increasing the distance between patient OB and grating G1, which however, increases the magnification and thus reduces the size of the field of view. In addition, the inverse geometry allows using gratings G2 of comparably lower quality compared to the earlier non-inverse grating arrangements. Again this allows cutting production overhead. Also, the mounting for the grating pack G1, G2 is no longer in front of the patient but is positioned behind him or her as pack G0 and G1. The inverse arrangement allows for improved ergonomics as this may help, especially claustrophobically inclined patients, to feel more comfortable during the scan operation. In the FIG. 6 embodiment the gratings G0 and G1 are now mounted rigidly to together and remain parallel with the G2 grating at all times during the acquisition. In other words, the pack G1, G2 rotates in concert with the grating G2 at the other end of the arm. As before the X-ray source XR may or may not be rotatable. Although not shown, a rotatable pre-collimator CP can be used in a similar manner as described above.

Although in the embodiments as per FIG. 1-6, a curved scan path was described, this may not be so necessarily for all embodiments.

Figure 7:
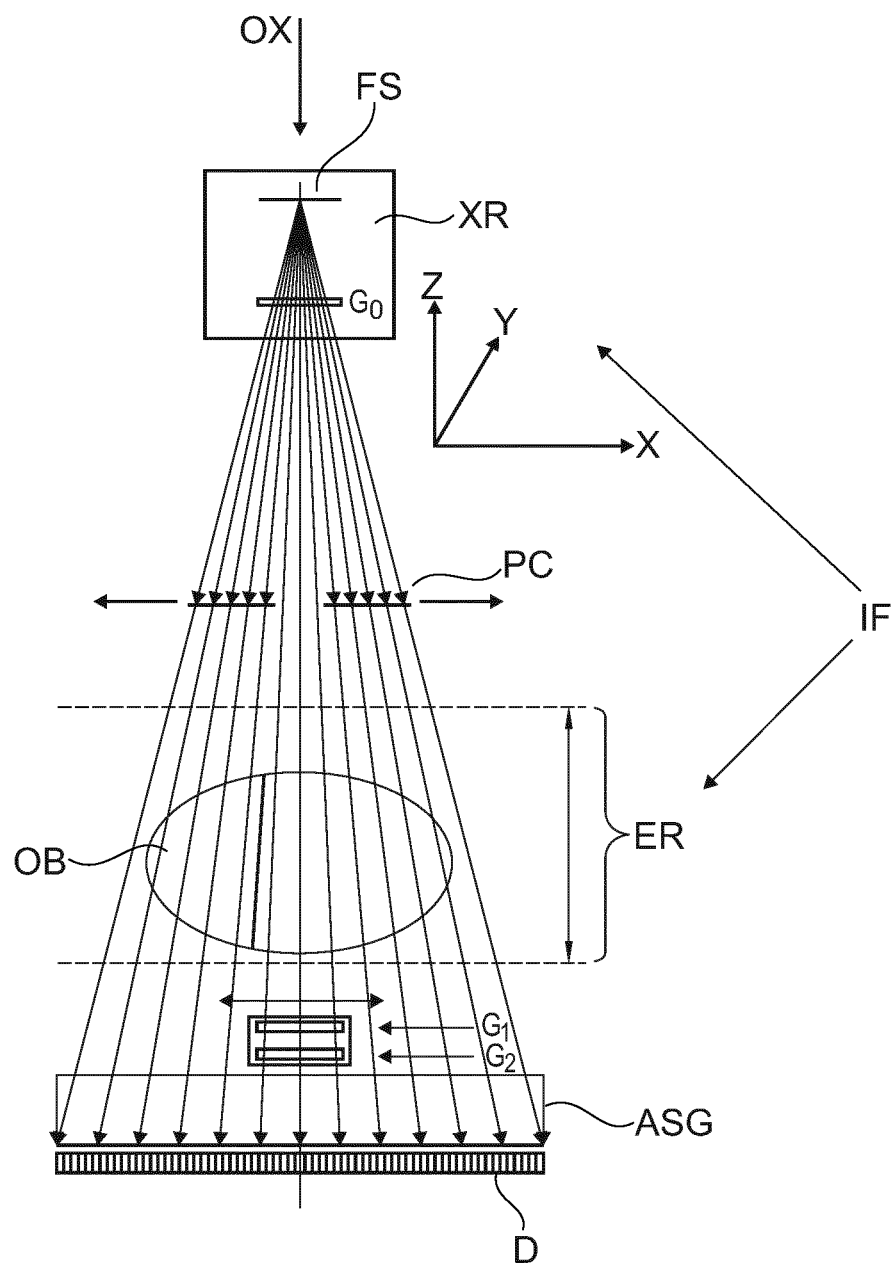
FIGS. 7-10 show different further embodiments of an X-ray imaging apparatus with stationary X-ray detector and with linear (i.e. non-curved) grating scan paths.

For instance, referring to the embodiment of FIG. 7, which is similar to the embodiment in FIG. 1 where the patient is expected to lie during the image acquisition, the grating pack G1, G2 is now arranged to sweep out a linear scan path parallel to the X-ray detector D and source grating G0 at an appropriate distance. Both X-ray source and source grating remain stationary relative to a given orientation of the optical axis. In particular, in the embodiments with linear scan motion, no motion of X-ray source and/or source grating is required if the source grating is large enough to illuminate the entire X-ray detector. To ensure that the X-ray is confined to the footprint of the linearly moving grating pack G1, G2 there is a pre-collimator PC in between the object and the grating G0 whose aperture moves parallel to the X-ray detector and in such a way that the slit remains opposite the X-ray detector pack at all times.

Figure 8:
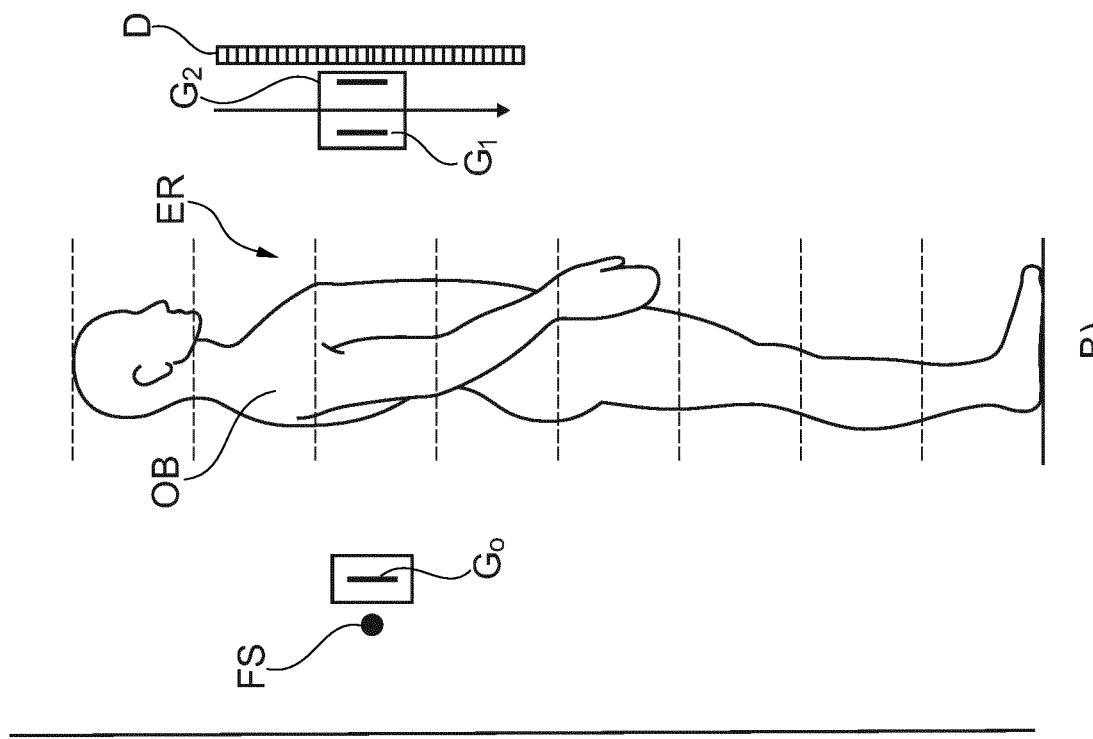
Figure 8:
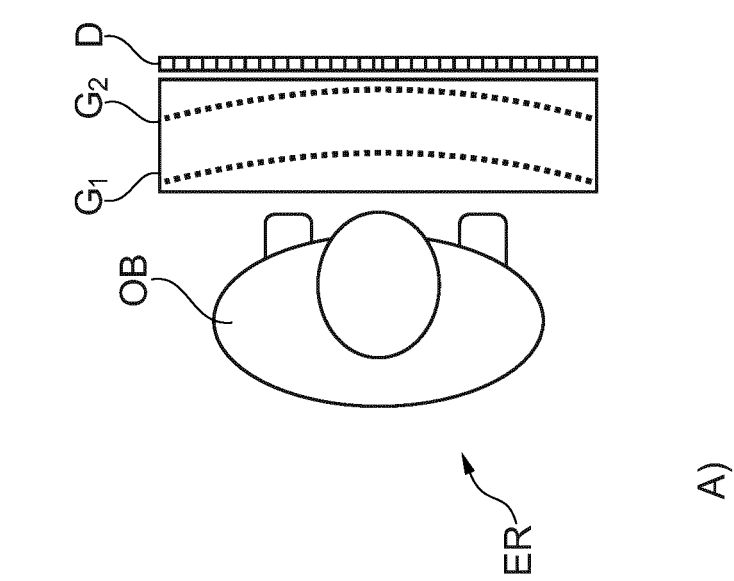

Referring now to FIG. 8, this shows a variant to the embodiments as per FIGS. 3, 4, but this time with a linear scan path. To achieve this, the rulings of gratings G1 and G2 and that of G0 are aligned along the scan direction (in this case, vertical scan direction). In other words, the rulings extend into the drawing plane of FIG. 8. Because the rulings of the gratings are run parallel to the scanning direction, it is possible to keep source grating G0 fixed and to only move grating pack G1, G2 pack along the linear trajectory. To achieve good image quality it is envisaged in one embodiment to have at least one, preferably all of the gratings G1, G2 and G0 arranged in a focused fashion for alignment of the gratings' trench directions towards the focal spot FS. In other words, the trenches are not formed as parallel "troughs" in the material as in the foregoing embodiment, but are slightly tilted with respect to each other as to together point to the focal spot from different directions. In the view as per FIG. 8, where one views along the trenches, one can see that they together follow a curved outlay indicated by the dotted lines. Alternatively, it may be possible to achieve this focused arrangement by using a substrate (possibly from a material other than silicon) that allows for easier bending, such as Kapton. The trenches may then be formed in parallel, and then the substrate is slightly bended to achieve the alignment with the focal spot.

Figure 9:
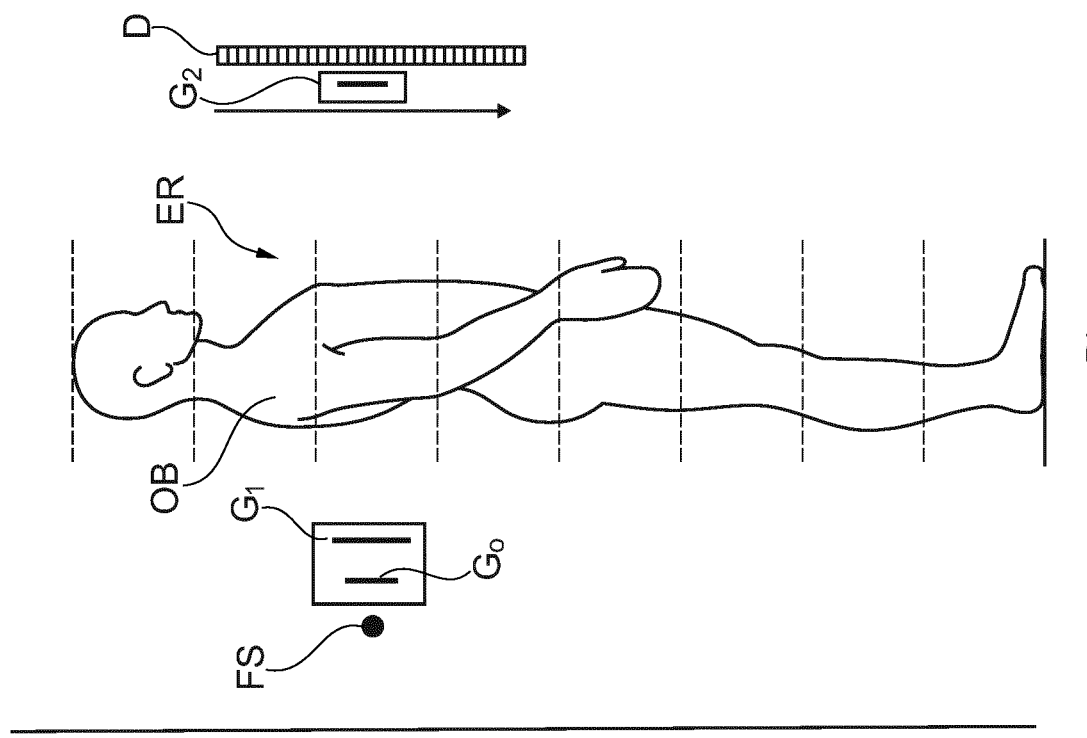
Figure 9:
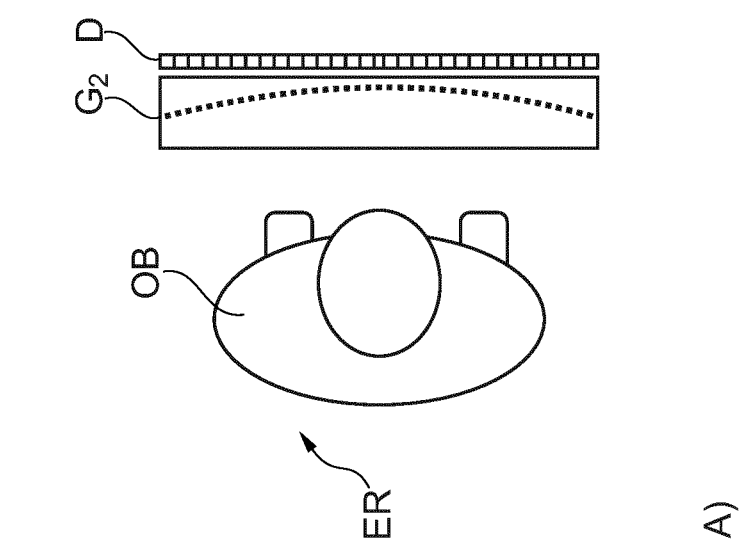
Figure 9:
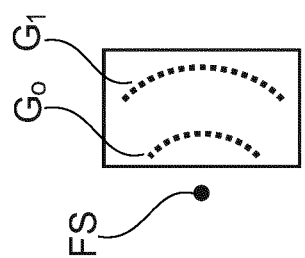

The embodiment in FIG. 9 is a variant of FIG. 8 with inverse grating arrangement similar to what has been explained before at FIG. 6. In other words, it is now only grating G2 that performs a scan operation along in a linear trajectory whilst both G1 and G0 remain stationary with respect to each other. Also the patient is now arranged between G1 and G2 rather than the patient being outside the space between G1 and G2 as previously in FIG. 6. Again, to ensure good image quality the rulings extend along the scan direction, in this case horizontally whilst G0 and G1 are rigidly kept stationary. The rulings in G2 again are preferentially formed in a focused fashion as explained before at FIG. 8.

Figure 10:
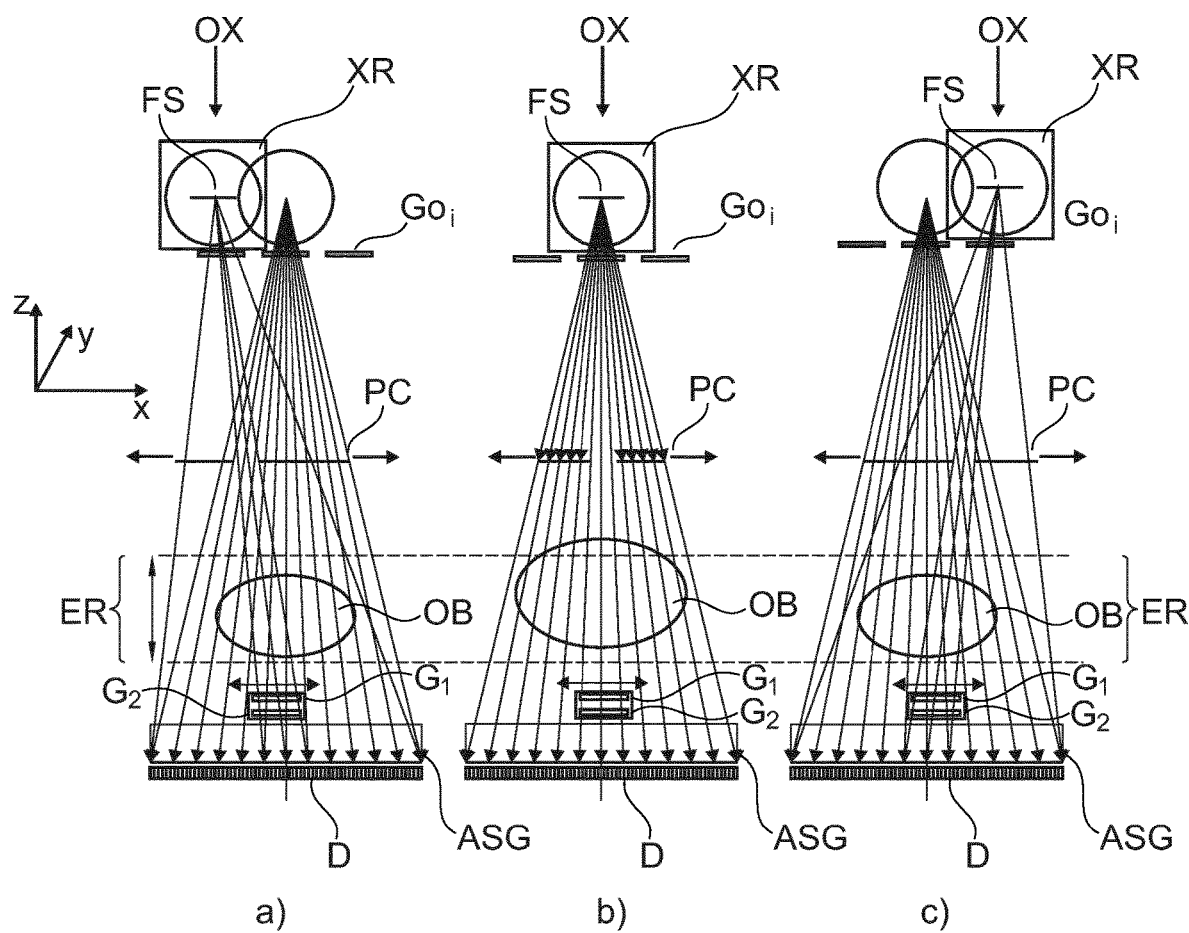

With reference to FIG. 10 there is shown a variant of the FIG. 7 embodiment. The embodiment as per FIG. 10 shows an X-ray apparatus that is capable of performing tomosynthesis imaging although the same tomosynthesis capability can be afforded also for the embodiments as per FIGS. 8, 9. X-ray tomosynthesis imaging is an X-ray projection technique, which provides z-dependent information from the sample. Successive projection images are taken at different angles of the X-ray beam, which passes the object OB. The projection data collected from different angular positions is reconstructable by an appropriate tomosynthesis reconstruction technique into a 3-dimensional representation in of the three contrasts (phase, attenuation or dark-field) of the material distribution of the object OB. In FIG. 6, the tomosynthesis capability of the grating scanning X-ray apparatus is sketched. In essence, the X-ray tube or at least its focal spot FS unit is moved to different X- or Y positions.

More specifically, and in addition to what has been described before at FIG. 7, in the FIG. 10 embodiment, at least the focal spot (not necessarily the whole X-ray source XR) is arranged to move in discrete steps along an X-ray scan path parallel to the scan motion of the grating pack G1, G2. However gating pack G1, G2 and focal spot do not move together, but said motions alternate. That is, the X-ray source moves to a particular spot along the X-ray path, stops there and then the grating pack G1, G2 is scanned over the X-ray detector as described in the other embodiments in FIGS. 7-9, to acquire image data for this spot or "perspective view" only. Upon completion of the grating pack G1, G2 scan, the focal spot then moves on to the next spot and the grating scan is repeated, this time for this, second, spot and so on. For a tomosynthesis, two, preferably three or even more, suitably spaced spots are sufficient. A suitable actuator is used to effect motion of focal spot or the whole XR ray tube assembly.

In one embodiment there is a single grating G0 that moves with the linearly translating X-ray source or focal spot FS. However, in a preferred embodiment as shown in FIG. 10, the source grating itself is not moved. Rather, a plurality of source gratings $G0_i$, for instance but necessarily i=3, as shown in FIG. 10, are laid out in linear fashion. The X-ray source then moves from grating $G0_i$ to grating $G0_{i+}1$ to assume different, in this case three different, angular positions, relative to the object OB and X-ray detector D, to collect projection image signals for the tomosynthesis. The plurality of source gratings G0i, two or more, can be arranged in a frame structure that is run, opposite the tube XR, in line of sight at a suitably adjusted distance from the egress window of the tube housing. The tube can either move within the housing or it is housing with the tube that moves in its entirety past the series of source gratings. In the earlier embodiment, the egress window is arranged long enough to extend the whole length of the grating series $G0_i$. It should be noted that the inverse grating structure explained above can also be used as an alternative for the embodiments as per FIGS. 1, 7 and 10.

Figure 11:
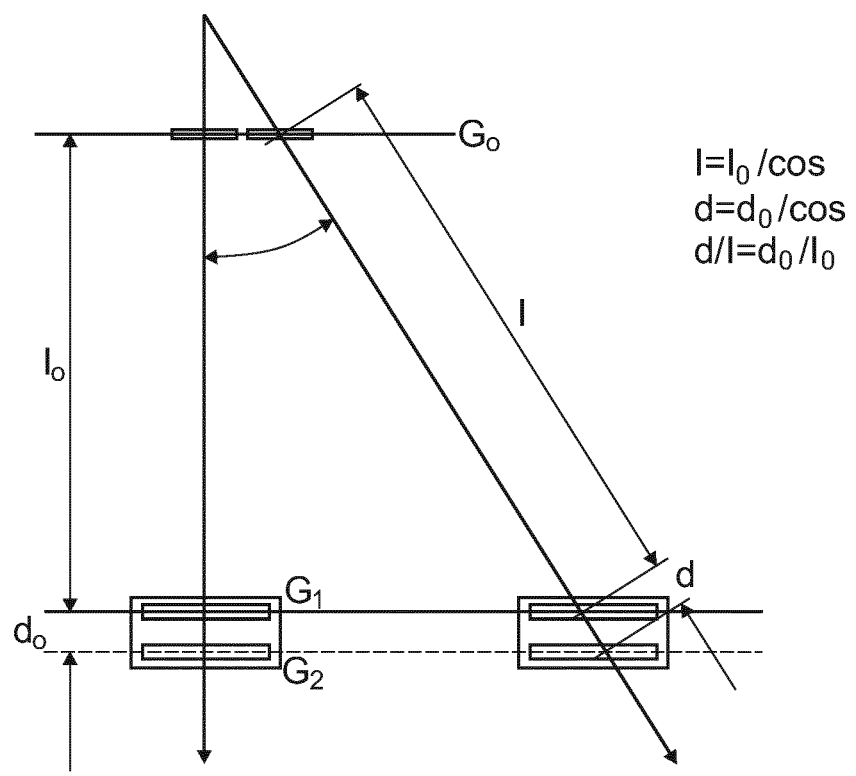
FIG. 11 shows the geometry of interferometric gratings in the context of linear scan movements.

FIG. 11 is an illustration of the geometrical underpinnings that make it possible to use linear scan paths. In fact, the reader may be surprised that the interferometric set-up still works when an inclined (in x-direction) illumination of the object is performed. But it has been found by Applicant, that with respect to the involved aspect ratios of the gratings G0, G1, G2, there is translation invariance in x-direction (direction of one of the X-ray detector edges), when the grating trenches are aligned in x. This invariance property of the interferometer G1, G2 system was also exploited in the above embodiments when scanning the G1/G2-interferometer unit IF in X or Y-direction past the fixed X-ray detector and fixed X-ray tube XR. As can be seen in FIG. 11, the intra-grating paths through the interferometer are not the same during a linear translation. Yet the Talbot set up requires that the certain fixed distances are maintained to achieve the Talbot pattern replication. However, Applicant discovered a geometric relationship that can be harnessed to our advantage in using linear scan paths because the changes of the respective paths during the linear scan cancel each other out exactly. More specifically and with continued reference to FIG. 11, path length through the interferometer will change when going from vertical to inclined illumination of the object. The path lengths involved here are the path $l_0$ ($G_0$ grating to $G_1$) and path $d_0$ ($G_1$ to $G_2$) for the case of vertical illumination. For inclined illumination, these path lengths are written as l and d, respectively. The lengths l and d increase by $l/\cos\theta$ when the illumination is changed to the inclined state ($\theta>0$); $d=d_0/\cos\theta$; $l=l_0/\cos\theta$. But what plays in our hands here is that main design rules concerning the interferometric setup bear a similar d/l relation such as:—

$$d_0/l_0 = p_2/p_0,$$

with $p_0$ and $p_2$ denoting the grating pitches of the G0 and the G2 grating respectively. Interferometric design rules specify via the path length and pitch relations, a certain energy bandwidth or "design energy" for the radiation where the "visibility" of the interference pattern is at its maximum. The design relation of $p_1$ (pitch of grating G0 and $p_2$ is given by:—

$$p_2 = p_1/2 \text{ (for plane wave relation) and by}$$

$$p_2 = p_1/2 * l/d/(l/d-1) \text{ (for spherical wave relation)}.$$

Here, only the ratio d/l or l/d shows up, too, and the influence of angle $\theta$ is cancelled.

A third relation links the design photon energy E or design wave length $\lambda$ ($E \sim 1/\lambda$) to the pitch $p_1$ of grating $G_1$:—

$$d \sim p_1^2/\lambda \sim p_1^2 * E$$

Here only d shows up. But, according to the $\cos\theta$-dependence of the effective path length d, the design energy shift incurred is small. For example, for a tomo-angle of $\theta=20°$, this amounts only to an increase of about 6% in design energy which is either negligible for present purposes or, if necessary, this small energy shift may be appropriately considered in the signal processing at reconstruction stage.

For completeness, it should be noted here, that the number and the orientation of the Moiré fringes do not depend on the orientation of the grating structures G1 and G2 (either parallel to X or Y or in between). That is, the number and orientation of the fringes are solely determined by a mutual detuning of the interferometer set up and $G_0$ grating. This is fact is also harnessed herein and makes the proposed use of fixed full view X-ray detectors possible.

It should be understood that the interferometric set up as explained above in the previous Figures can be built in as an add-on to ordinary existing X-ray imaging apparatus such as a mammography system or planar 2D radiography systems. Thanks to, in particular the dark-field channel, micro-calcification anomalies of the human breast can be studied. Also in chest X-Ray, cellular structure anomalies related to chronic obstructive pulmonary disease (COPD) of the lung can be examined, again thanks to the supplied dark-field imagery.

Also, the above described concept of using scanning interferometric gratings in combination with a stationary full view X-ray detector (having a radiation sensitive area larger than the area of interferometric grating(s)) is also envisaged herein for tomography (CT) scanning apparatuses. The above described set up and the above relations hold true for any given angular position of the optical axis which is rotating around the examination region (object OB) in CT context.

The concept of stationary full-field X-ray detector with scanning interferometer also simplifies signal processing when computing the images from the collected measurements. There is a different, simplified data redundancy introduced as compared to solutions with movable X-ray detectors that perform the scan. See for instance, T Koehler et al in "Slit-scanning differential X-ray phase-contrast mammography: Proof-of-concept experimental studies", Medical Physics 42, 1959 (2015) for such a solution. In such or similar scanning X-ray detectors, each image pixel position or "geometrical ray" is seen by a plurality of X-ray detector pixels and the hence the interferometric measurements are spread out across different readings from different X-ray detector pixels thus introducing said redundancy. Accounting for this data redundancy can be computationally costly. In contrast, in the proposed system there is a simplified redundancy due to a fixed one-to-one relationship between X-ray detector pixel and image pixel thanks to the stationarity of the X-ray detector during the data acquisition. In other words, a redundancy there still is with the proposed system, because each geometrical ray is still measured for at multiple times, but the measurement now record different Moiré patterns because of the interferometer IF movement.

Although in the above embodiments a dedicated second grating (G2) was used as an analyzer grating to form the interferometer, this may not necessarily be so in all embodiments. For instance, the analyzer grating G2 functionality can also be integrated into the X-ray detector D itself. What is more, the grating function can be entirely taken over by the X-ray detector itself by a judicial arrangement of the pixel geometry, in particular the inter-spacing between the pixels accordingly. This "hybrid" or "no-G2 grating" interferometer with a single grating G1 where parts of the X-ray detector structure are used to take play the role of the other gating can be used in any one of the embodiments as per FIGS. 3-6. In particular then, in this embodiment, it is not the whole of the interferometer that is moving but only the part G1 whereas the other part (now an intrinsic part of the X-ray detector) remains fixed.

To enhance the flexibility it should be noted that the interferometric equipment as arranged in the scan arm can be swung out altogether outside of the examination region around the focal spot so as to convert the X-ray image apparatus back to a traditional absorption image only X-ray set up. Of course, the multi-channel imaging always supplies the absorption image as this effect is accounted for when fitting to the forward model. However, swinging out the interferometric equipment altogether has the benefit of reducing computational costs to still arrive at the absorption image.

One exemplary dimension envisaged herein, which are purely exemplary, is a full field fluoroscopic X-ray detector D with width of about 43 cm and height of about 43 cm. Interferometric gratings G1, G2 used by Applicant is are about 5 cm×43 cm for instance 4.8 cm×43 cm or 5 cm×50 cm. The benefit of keeping the X-ray detector stationary at all times for any given optical axis orientation allows cutting down image blur. This in turn allows using X-ray detector electronic read-out rates that are lower than that ordinarily required for moving X-ray detector architecture. For instance a frame rate of 26 fps (frames per second) is sufficient which corresponds to about 10 readings per centimeter of scan so along an X-ray detector length about 50 cm length can be scanned in about five seconds. Of course a higher frame is welcome as this allows minimizing motion blur caused by patient movement for instance.

Although the above described embodiments, ceiling or floor mounted, that is residential, solutions have been described, mobile system are not excluded herein where the described components are mounted in a wheeled "dolly" carriage construction.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single item or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An X-ray imaging apparatus comprising:
   an X-ray source for emitting a beam of X-ray radiation;
   an X-ray detector arranged opposite said X-ray source across an examination region for accommodating an object to be imaged; and
   an interferometer located between the X-ray source and the X-ray detector, wherein the interferometer is arranged at least partly in the beam of X-ray radiation during operation for performing differential phase contrast imaging and/or dark field imaging, the interferometer comprising at least one grating to modulate onto said X-ray radiation an interference pattern detectable by said X-ray detector;
   wherein a footprint of said at least one grating is smaller than a footprint of a radiation sensitive area of said X-ray detector; and
   wherein during an imaging operation the apparatus is configured to move said at least one grating in a scanning motion across the X-ray detector whilst said X-ray detector remains stationary relative to the examination region.

2. The X-ray imaging apparatus as per claim 1, wherein one dimension of the footprint of the at least one grating is essentially coextensive with a corresponding dimension of the footprint of the X-ray detector.

3. The X-ray imaging apparatus as per claim 1, wherein the X-ray detector is a full-field X-ray detector.

4. The X-ray imaging apparatus as per claim 1, wherein the apparatus is configured to effect another motion of the at least one grating, different from the scanning motion.

5. The X-ray imaging apparatus as per claim 1, wherein during the imaging operation the apparatus is configured to effect a motion of the object relative to the at least one grating or the X-ray detector.

6. The X-ray imaging apparatus as per claim 1, wherein the interferometer includes another grating movable in the scanning motion, wherein the at least two gratings remain in a fixed spatial relationship relative to each other during the scanning motion.

7. The X-ray imaging apparatus as per claim 6, wherein the at least two gratings are arranged on mutually opposite sides of the examination region.

8. The X-ray imaging apparatus as per claim 6, wherein the at least two gratings are arranged on a same side of the examination region.

9. The X-ray imaging apparatus as per claim 1, wherein the scanning motion is performed along a straight path.

10. The X-ray imaging apparatus as per claim 1, wherein the scanning motion is performed along a curved path.

11. The X-ray imaging apparatus as per claim 1, wherein the X-ray detector has a monolithic structure.

12. The X-ray imaging apparatus as per claim 1, wherein the X-ray source is configured to move along a path substantially parallel to the scanning motion.

13. The X-ray imaging apparatus as per claim 12, further comprising a plurality of source gratings arranged substantially parallel to the path along which the X-ray source is movable.

14. The X-ray imaging apparatus as per claim 1, wherein the scanning motion is at least one of vertical and horizontal.

15. The X-ray imaging apparatus as per claim 1, wherein rulings of said at least one grating extend in a direction substantially parallel or substantially perpendicular to the scanning motion.

* * * * *